United States Patent [19]

Holzhauer et al.

[11] Patent Number: 5,068,406
[45] Date of Patent: Nov. 26, 1991

[54] COMPARTMENTED OXIDATION METHOD

[75] Inventors: Juergen K. Holzhauer, Naperville; Albert P. Brown, Downers Grove; Aubrey C. Reeve, Warrenville, all of Ill.

[73] Assignee: Amoco Corporation, Chicago, Ill.

[21] Appl. No.: 561,063

[22] Filed: Aug. 1, 1990

Related U.S. Application Data

[62] Division of Ser. No. 403,769, Sep. 6, 1989.

[51] Int. Cl.$^5$ .......................................... C07C 51/265
[52] U.S. Cl. .................................. 562/413; 562/414; 562/416; 562/417
[58] Field of Search ............... 562/413, 414, 416, 417

[56] References Cited

U.S. PATENT DOCUMENTS

| | | | |
|---|---|---|---|
| 4,159,307 | 6/1979 | Shigeyasu et al. | 422/215 |
| 4,241,220 | 12/1980 | Itaya et al. | 562/414 |
| 4,593,122 | 6/1986 | Hashizume | 562/414 |
| 4,769,487 | 9/1988 | Hundley et al. | 562/413 |

*Primary Examiner*—Paul J. Killos
*Assistant Examiner*—Vera C. Clarke
*Attorney, Agent, or Firm*—Gunar J. Blumberg; William H. Magidson; Ralph C. Medhurst

[57] ABSTRACT

An apparatus and a method for continuously oxidizing an aromatic alkyl in the liquid phase and under oxidation reaction conditions, for the purpose of producing a desired aromatic carboxylic acid product, is disclosed. A seriatim arranged array of reactor compartments, each of which is adapted to accommodate a gaseous phase as well as a liquid phase is contemplated. Means for separately adjusting the reaction mixture composition of each reaction compartment is provided.

16 Claims, 3 Drawing Sheets ns 5,068,406

COMPARTMENTED OXIDATION METHOD

This is a division of application Ser. No. 403,769, filed Sept. 6, 1989.

TECHNICAL FIELD OF THE INVENTION

The present invention is generally directed to a method and to an apparatus for continuously oxidizing an alkylaromatic in the liquid phase and under oxidation reaction conditions to produce an aromatic carboxylic acid. The method and the apparatus each make use of a compartmented oxidation reactor to produce the aromatic carboxylic acid.

BACKGROUND OF THE INVENTION

Continuous stirred tank reactors offer distinct advantages over batch-type reactors for a wide variety of hydrocarbon oxidations, such as those involving gas-liquid reactions as well as those involving gas-liquid-solid reactions. For example, it is generally the case that the capital investment expenses as well as the operating costs are typically relatively lower for a conventional continuous stirred tank reactor than for a conventional batch-type reactor of comparable throughput.

There are certain instances, however, where a batch-type reactor is preferred over a continuous stirred tank reactor. For example, in the manufacture of certain aromatic carboxylic acid products, it is well known that the presence of the product causes inhibition of the oxidation reaction itself, depending upon the concentration of the products within the reaction mixture. Thus, in many instances involving product-inhibited oxidation reactions the utilization of a single stirred tank reactor cannot provide the high yields desired because of the presence of a relatively higher concentration of the inhibiting product during much of the oxidation reaction period. While a batch-type reactor offers one advantage over a continuous stirred tank reactor in this regard, in that the inhibiting product is typically not present in sufficient reaction-inhibiting concentration until towards the end of the reaction, certain disadvantages of utilizing batch-type reactors generally favor utilization of a continuous stirred tank reactor, if at all possible. For example, it is well known that product quality generally varies from batch-to-batch. Occasionally, the variation in product quality renders the product unacceptable for its intended purpose. Also, it is generally well recognized that batch-type operations typically involve relatively greater manpower expenses and batch-type reactors are typically larger than continuous reactors for the same throughput.

While it is possible to connect a large number of continuous stirred tank reactors in series to achieve desired reaction kinetics, to do so is not economically practical from the standpoint of capital-investment and operating cost considerations.

Liquid phase oxidation of an alkylaromatic is exothermic. Certain conventional processes for oxidizing an alkylaromatic in the liquid phase employ a reaction mixture which includes a solvent. In such processes, a desired reaction temperature is achieved by maintaining the oxidation-reactor internal pressure at a value such that evaporation of a portion of a reaction mixture occurs at a desired rate. The thus-vaporized portion of the reaction mixture is then passed from the oxidation reactor to a condenser which serves to remove heat of reaction and to condense at least a portion of the reaction-mixture vapor supplied thereto. The condensate that it produced is then typically returned to the reactor as reflux.

The liquid phase oxidation of aromatic alkyls to aromatic carboxylic acid products is currently of significant commercial importance. It is accordingly highly desirable to improve the yield and quality of aromatic carboxylic acid products.

SUMMARY OF THE INVENTION

One aspect or feature of the present invention is directed to a method for continuously oxidizing an alkylaromatic in the liquid phase and under oxidation reaction conditions to produce an aromatic carboxylic acid. The method comprises sequentially passing at least a portion of a reaction mixture comprising the alkylaromatic through a plurality of a series-arranged walled but communicating compartments of an oxidation reactor under predetermined oxidation reaction conditions, from an initial one of the series-arranged walled plural compartments to a terminal one thereof, optionally introducing the remainder portion of the reaction mixture or one or more reaction mixture components in one of the series-arranged walled plural compartments downstream from the initial compartment, and passing the introduced remainder portion sequentially to the terminal compartment, while agitating the contents of each of the walled plural compartments to produce in each of the walled compartments an aromatic carboxylic acid-containing liquid phase and a gaseous phase. At least a portion of the walls of the series-arranged compartments are apertured to enable passage of the reaction mixture through the oxidation reactor from the initial one of the series-arranged plural compartments to the terminal one thereof. The liquid phase temperature in each of the walled plural compartments is monitored and controlled, if desired. The gaseous phase contained within the terminal compartment is withdrawn. At least a portion of the thus-withdrawn gaseous phase is then condensed to produce a liquid stream. At least a portion of the thus-condensed liquid stream is then apportionably returned to preselected ones of the walled plural compartments in a controlled manner so as to maintain a preselected liquid-phase temperature differential between the terminal and initial compartments of the oxidation reactor.

Another aspect or feature of the present invention is directed to an apparatus for continuously oxidizing the alkylaromatic in the liquid phase and under oxidation-reaction conditions to produce the aromatic carboxylic acid product. Such an apparatus, as well as still other aspects and/or features of the present invention, are discussed hereinbelow.

BRIEF DESCRIPTION OF THE DRAWINGS

In the drawings.

Throughout the drawings, like reference numerals refer to like parts.

DETAILED DESCRIPTION OF THE PREFERRED EMBODIMENTS

Figure 1:
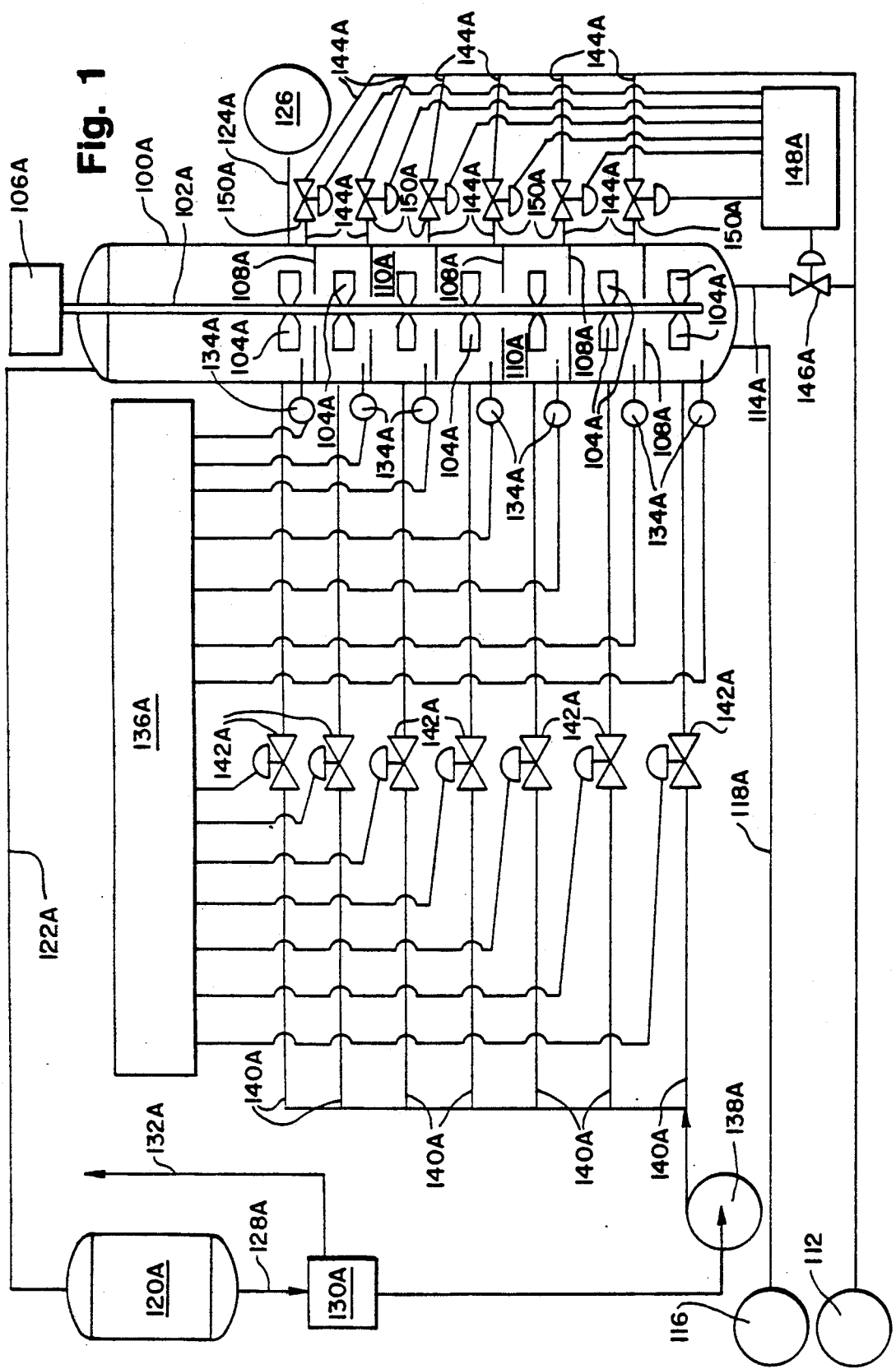
FIG. 1 is a process flow diagram that depicts a system embodying the principles of the present invention.

Referring to FIG. 1, there is shown a system and apparatus for continuously oxidizing an alkylaromatic in the liquid phase and under conditions that produce an aromatic carboxylic acid product.

A generally cylindrical oxidation reactor 100A, oriented vertically along a central, vertical axis, includes an agitator shaft 102A that is disposed generally along the reactor central axis. The agitator shaft 104A is affixed thereto and is driven by a commerically available drive mechanism 106A.

Internally, reactor 100A further includes several spaced-apart, centrally apertured dividers or partitions 108A, each of which is disposed in a generally horizontal plane. The aperture in each such divider 108A is positioned as to enable the agitator shaft 102A to be disposed generally through the central portion of each such divider 108A and to allow reactor contents to flow between each such divider 108A and the agitator shaft 102A. Adjacent dividers 108A are so spaced as to accommodate a set of impeller blades 104A to be disposed therebetween. Each such set of impeller blades 104A rotates generally in a horizontal plane when driven by drive mechanism 106A.

The reactor 100A thus defines internally a plurality of series-arranged walled compartments 110A which are disposed along the central longitudinal axis of the reactor.

An alkylaromatic feed stream to the reactor 100A from a source 112 is fed by a feed pipe 114A, and an oxidizing gas from a source 116 is fed by a feed pipe 118A, into the initial one of the series-arranged walled plural compartments in reactor 100A. In a preferred embodiment, oxidizing gas inlet means are added to each of the series-arranged walled compartments of the reactor wherein the amount of oxidizing gas added to each of said compartments can be independently controlled. Commercially available gas flow controllers may be used to achieve desired, pre-selected oxidizing gas flow rates for each of said compartments. For example, referring to the embodiment in FIG. 1, instead of running directly to the initial compartment as shown, line 118A would branch and run separate lines to each compartment shown. Each branch line, including the one to the initial compartment, would then have a separate commercially available gas flow controller for independently controlling the flow of oxidizing gas to the respective compartment. The alkylaromatic feed source 112 and the oxygen-containing gas source 116 each include separate fluid and gas transfer means (not shown), for passing the thus-introduced alkylaromatic feed stream and oxygen-containing gas to the terminal one of the plural compartments.

The alkylaromatic feed and other reaction components, along with the oxygen-containing gas, move upwardly through the reactor 100A, passing from one compartment 110A to an adjacent reactor compartment 110A located immediately thereabove, eventually passing to a terminal one of the series-arranged walled plural compartments 110A. As the alkylaromatic feed and oxygen-containing gas pass upwardly through the plural compartments 110A, the aromatic carboxylic acid product is produced. The internal pressure of the oxidation reactor 100A is preselected for producing, under predetermined oxidation-reaction conditions in each of the walled plural compartments 110A, an aromatic carboxylic acid-containing liquid phase and an oxygen-containing gaseous phase. Because the dividers 108A are apertured, adjacent compartments 110A are thus in phased communication with one another.

Rotation of the impeller blades 104A about the central axis of the reactor 100A and relative to the internal wall surface of the reactor 100A causes the contents of each of the walled plural compartments 110A to circulate about the reactor's central axis relative to the reactor inner surface. This, in turn, causes disentrainment of the liquid phase from the gaseous phase by centrifugal force within each of the walled plural compartments 110A. However, in some or all of the reactor compartment baffles can be placed on the internal wall surface to suppress the rotation of the reactor contents and improve the mixing therein. These baffles may be of any size and shape. For example, while a baffle made with a circular cross-section could be used, this shape would be less efficient than a baffle with a rectangular cross-section but would allow for some rotation of the liquid to aid disentrainment while retaining some of the desirable features of baffles by providing mixing and air dispersion.

The oxidation reaction is exothermic. To control reaction temperature, a portion of the product-containing reaction mixture is allowed to vaporize. The vaporized portion of the reaction mixture is passed from the terminal or downstream-most one of the series-arranged walled plural compartments to a condenser 120A via a discharge pipe 122A. From the terminal reactor compartment the product-containing reaction mixture is passed via discharge pipe 124A to a collection site 126 for further processing, as desired.

Process vapors are condensed in condenser 120A and enter, via conduit 128A, separator 130A which separates non-condensable gases from the now-condensed process vapors. The non-condensable gases are vented via vent line 132A. The condensed process vapors are returned back into reactor 100A as reflux.

To optimize the reaction of alkylaromatic to aromatic carboxylic acid, it is desirable to control the temperature of the reaction mixture internally along the entire length of the reactor. Accordingly, the reactor 100A includes a plurality of commercially available temperature transducers 134A, each such temperature transducers 134A having a temperature sensing element that is disposed within the corresponding one of the plural reactor compartments 110A. Each one of the plural temperature transducers 134A is operatively connected to a commercially available process controlled system 136A and senses the liquid-phase temperature of the reaction mixture within the corresponding compartment.

Condensed process vapors from separator 130A are returned as reflux back into reactor 100A by transfer pump 138A.

A plurality of return lines 140A are supplied by transfer pump 138A. Each one of the plural return lines 140A returns as reflux a portion or all of the condensed process vapors, as necessary, to a corresponding one of the plural walled compartments 110A. Each such reflux return line 140A includes an automatic flow control valve 142A, operatively connected to the process control system 136A, for controlling flow of condensed process vapors that are being refluxed to a corresponding one of the plural walled compartments 110A. Generally, the thus-condensed liquid stream is apportioned and returned to the plural walled compartments 110A so as to maintain a preselected liquid-phase temperature differential along the reactor between the terminal and initial compartments. Transfer pump 138A in fluid communication with the reactor 100A, thus assists in passing the refluxed reaction mixture to the final or terminal one of the plural walled compartments 110A.

The alkylaromatic feed stream, mentioned above, may include solvent or solvents and catalyst, or the solvent and the catalyst may be added separately to each compartment.

Suitable solvents for use in the method of this invention include any $C_2$–$C_6$ fatty acids such as acetic acid, propionic acid, n-butyric acid, isobutyric acid, n-valeric acid, trimethylacetic acid and caproic acid and water and mixtures thereof. Preferably, the solvent is a mixture of acetic acid and water, which more preferably contains from 0.5 to 20 weight percent of water, as introduced into the oxidation reactor.

Suitable catalysts for use include any catalyst system conventionally used for liquid phase oxidation of alkyl aromatically and preferably include the catalyst metals comprising cobalt and manganese, and a bromine source. Zirconium compounds may also be added as catalyst metals.

Such bromine sources include elemental bromine ($Br_2$), or ionic bromide (for example, HBr, NaBr, KBr, $NH_3Br$, etc.), or organic bromides which are known to provide bromide ions at the operating temperature of the oxidation (e.g., bromobenzenes, benzylbromide, mono-and di-bromoacetic acid, bromoacetyl bromide, tetrabromoethane, ethylenedibromide, etc.).

As mentioned above, a portion or all of the alkylaromatic feed stream is introduced into the initial compartment of the reactor 100A via feed pipe 114A. If only a portion of the alkylaromatic is added to the first compartment, the remainder of the alkylaromatic feed stream can be selectively fed to any one of the series-arranged compartments 110A via the inlet pipes 144A.

The feed pipe 114A can include an automatic flow control valve 146A operatively connected to a second process control system 148A, and each of the inlet pipes 144A can include an automatic flow control valve 150A operatively connected to the second process control system 148A, for passing at least a portion of the reaction mixture comprising the alkylaromatic through the plurality of series-arranged walled compartments 110A and for selectively introducing the remainder portion of the reaction mixture into another one, or into other ones, of the series-arranged walled plural compartments.

A preferred embodiment of the instant invention also comprises a method and an apparatus for apportioning the solvent or solvents, catalyst components and oxidizing gas independently to each of the series-arranged walled compartments. The reaction mixture composition of each reactor compartment may, therefore, be individually adjusted to achieve optimal results for oxidation of the selected alkylaromatic.

Thus the reactor means of this invention further comprises inlet means for separately introducing, in preselected amounts, reaction solvent, alkylaromatic, catalyst metals, and bromine source to each of the series-arranged walled but communicating compartments. This is accomplished, for example, by employing additional feed source means separately for the catalyst metals, bromine source and solvent. The catalyst metals, bromine source and solvent may be separately added to the reactor and individual reactor compartments utilizing a method or means equivalent to that depicted in FIG. 1 for the addition of the alkylaromatic, including additional feed pipes to each compartment, additional automatic flow control valves and process control systems for apportioning the solvent, catalyst metals or bromine source separately and in preselected amounts to each reactor compartment.

For example, in one preferred embodiment all or essentially all of the reaction solvent, catalyst metals and bromine source are added to the initial reactor compartment and it is the alkylaromatic that is apportioned to some or all of the reactor compartments. In still another preferred embodiment the catalyst components, which may comprise a cobalt compound, a manganese compound, a zirconium compound and a bromine source, are separately apportioned in preselected amounts among the reactor compartments. Thus it may be desirable to separately add some of the bromine source, or some of the manganese or cobalt or zirconium compounds to one or more downstream compartments to achieve optimal results for a given alkylaromatic feedstock. The compartmented design of the reactor of this invention with the flexibility to separately add alkylaromatic, solvent, catalyst metals and bromine source is an advantage of the instant process and apparatus and it permits the adjustment of the reaction composition within each compartment to be optimized for a specific alkylaromatic. It follows that there are many variations of reactor compartment composition that can be achieved by utilizing the reactor design and method of this invention. This versatility is a substantial improvement over prior processes and reactors.

Figure 2:
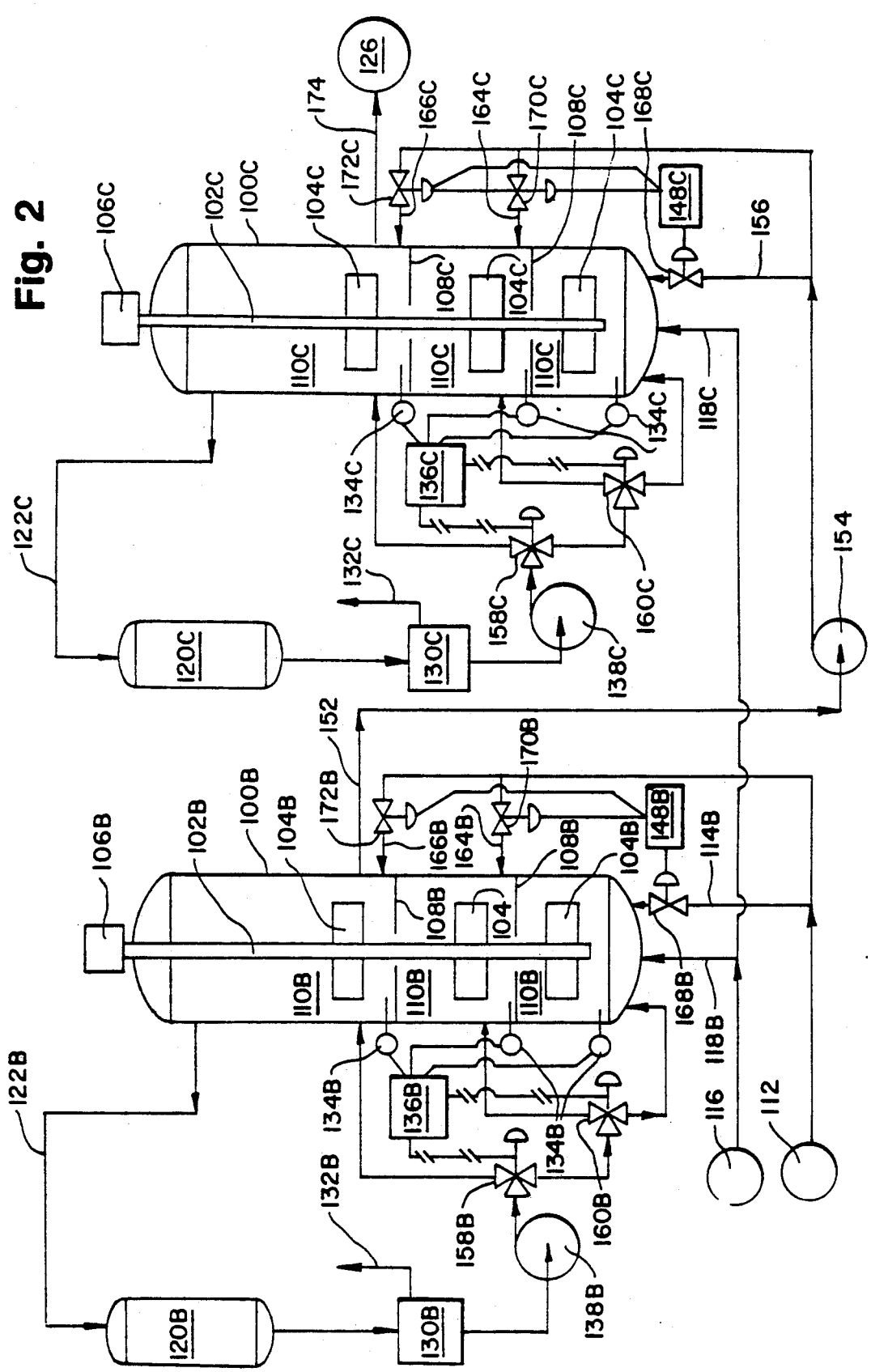
FIG. 2 is a schematic representation of one preferred system embodying the principles of the present invention.

In FIG. 2, a novel reactor configuration that has proven itself particularly useful for certain gas-liquid or gas-liquid-solid reactions, especially hydrocarbon oxidation reactions, is disclosed.

As mentioned above, a continuous stirred tank reactor generally offers distinct advantages over a batch-type reactor when effecting hydrocarbon oxidation reactions. Initial cost of a continuous stirred tank reactor is typically lower than that for a batch-type reactor of comparable throughput. Continuous stirred tank reactor volume is generally utilized more efficiently than is the reactor volume of a batch-type reactor. Variation of product quality, which is typically undesirable, occurs much more frequently in batch-type reactors than in a continuous stirred tank reactor. Also, operational expenses are generally higher for a batch-type reactor than for a continuous stirred tank reactor at a given throughput rate.

However, in the oxidation of certain alkylaromatics such as the oxidation of pseudocumene to trimellitic anhydride (or acid), where certain product-inhibited reactions are experienced, batch reactors are generally utilized. In the oxidation of pseudocumene to trimellitic acid using heavy metal catalysts, the trimellitic acid product complexes to and thereby deactivates the metal catalysts and inhibits the reaction. The reason that batch reactors are used to effect such hydrocarbon oxidation reactions is that the desired oxidation reaction, at least up to the advent of our invention, has generally not been able to be carried out to the desired degree of conversion in a single continuous stirred tank reactor (CSTR) because of the presence of the reaction-inhibiting product. The use of a pair of CSTR's has been similarly unavailing. That is, the concentration of the reaction-inhibiting product, which can be either a desired product or an undesired by-product of the desired hydrocarbon oxidation reaction, is typically so great as to inhibit production of the desired product.

With the present invention, on the other hand, the desired degree of conversion of product-inhibited oxidation reactions can be readily effected in continuous stirred tank reactors. It has been demonstrated, for example, that pseudocumene can be continuously oxidized to desirable, high yields while utilizing continuous stirred tank reactors 100B and 100C compartmentalized by apertured, substantially horizontally-arranged dividers 108B and 108C. The oxidation reactors 100B and 100C are connected to one another in series. Each reactor 100B and 100C is provided with apertured, horizontal dividers 108B and 108C to provide three walled compartments 110B and 110C for each of the reactors 100B and 100C.

Each reactor 100B and 100C is also provided with a centrally located and vertical disposed agitator shaft, 102B and 102C, that is driven by a respective, commerically available drive mechanism 106B and 106C, respectively. Impeller blades 104B and 104C, affixed to each of the agitator shafts 102B and 102C, respectively, are arranged along the length of the agitator shaft 102B and 102C and disposed generally radially outwardly therefrom, so as to provide means for circulating the contents of each of the walled compartments relative to the inner surface of the reactor 100B and 100C. In the reactor 100B and 100C, a gap or aperture is provided between the agitator shaft 102B and 102C, and each of the horizontal dividers 108B and 108C surrounding such agitator shaft 102B and 102C. Such a gap or aperture allows upward flow of contained liquid and gas (or vapor) within each reactor. FIG. 2 thus schematically depicts a six-stage, sequentially-arranged, compartmented continuous stirred tank reactor apparatus for effecting desired hydrocarbon oxidation.

In the oxidation of pseudocumene to produce trimellitic anhydride (or acid) it is desirable that that the liquid feed comprise pseudocumene as alkylaromatic hydrocarbon reactant, water and acetic acid as solvent, and a catalyst. In the oxidation of pseudocumene to trimellitic acid, such a catalyst typically comprises cobalt, manganese, zirconium and bromine.

In one preferred method of operation, all of such liquid feed from the alkylaromatic feed source 112 is introduced into the bottom compartment of the first reactor 100B via feed pipe 114B. An oxygen-containing gas from the oxygen-containing gas source 116 is concurrently introduced into the bottom of both reactors 100B and 100C via respective feed pipes 118B and 118C. In each reactor 100B and 100C vapor is separated from liquid. The thus-separated vapor is next passed from the uppermost or downstream-most compartment via respective discharge pipes 122B and 122C to a respective condenser 120B and 120C, respectively.

In the first reactor 100B, the partially-reacted liquid reaction mixture, comprising the trimellitic anhydride product, is discharged from the uppermost compartment via discharge pipe 152, and is passed via transfer pump 154 and via inlet pipe 156 into the bottom compartment of the second reactor 100C.

Because this oxidation of pseudocumene is an exothermic reaction, heat of reaction is controlled by vaporizing a portion of the reaction mixture. Off gas and reaction mixture vapors from reactors 100B and 120C are respectively passed to condensers 120B and 120C, each of which produce non-condensables as well as condensed process vapors.

The non-condensables exiting the first condenser 120B are separated from process condensate by separator 130B which vents a non-condensable off gas via vent line 132B, and passes the process condensate to return pump 138B which, in turn, returns the process condensate to the first reactor 100B as reflux. Similarly, exiting the second condenser 120C, the non-condensables are separated from the process condensate by separator 130C which vents the non-condensable off gas via vent line 132C and passes the process condensate to return pump 138C which returns the process condensate to the second reactor 100C, as reflux, as will be described in greater detail hereinbelow.

On the one hand, it is desirable to maintain the oxygen concentration in the vent gas at, or below, a predetermined concentration for certain safety reasons. On the other hand, it is desirable in oxidizing an alkylaromatic to maintain a relatively high oxygen concentration throughout the reaction mixture for purposes of optimizing product conversion and yields. High oxygen partial pressure also reduces the formation of undesirable colored by-products by suppressing coupling reactions. In a conventional hydrocarbon oxidation reactor, the vent-gas oxygen-concentration safety consideration, typically limits the particular oxygen concentration level that can be achieved within the conventional purposes. In practicing the present invention, however, it has been observed that a relatively highest oxygen concentration can be maintained in, for example, the lower two compartments of each of the reactors 100B and 100C, relative to a conventional reactor, while a particular off-gas oxygen concentration is maintained for safety reasons.

It has also been found that desirable reaction controls can be effected by apportioning the returned process condensate among the walled compartments of the reactors 100B and 100C. That is, the process condensate is controllably split and returned as reflux to the respective walled compartments 110B and 100C of each reactor 100B and 100C as dictated by process considerations. Such reflux split, for example, can be based upon certain desired temperature differences between adjacent compartments.

Referring to the first reactor 100B in the embodiment of FIG. 2, a first three-way valve 158B is operatively connected to the process control system 136B and controllably returns process condensate as reflux, either to the uppermost compartment or to a second three-way valve 160B. The second three-way valve 160B, also operatively connected to the process control system 136B, in turn, controllably returns process condensate, as reflux, either to the intermediate compartment or to the lowermost compartment. Each of the compartments of the reactor 100B is provided with a liquid-phase temperature-sensor 134B operatively connected to the process-control system 136B. In operation, that fraction of process condensate that is refluxed to any one compartment of the reactor 100B is controlled to maintain preselected liquid-phase temperature differentials between adjacent compartments, thereby also maintaining a desired liquid-phase temperature differential between the lowermost and uppermost reactor compartments. Accordingly, the thus-condensed liquid stream is apportioned among and returned to the plural, walled compartments so as to maintain a corresponding plurality of preselected liquid-phase temperature differentials having a predetermined magnitude.

The second reactor 100C is similarly equipped with a transfer pump 138C, first and second three-way valves 158C and 160C, temperature-transducers 134C, and a process-control system 136C, for maintaining a desired liquid-phase temperature differential between the lowermost and uppermost compartments.

Figure 3:
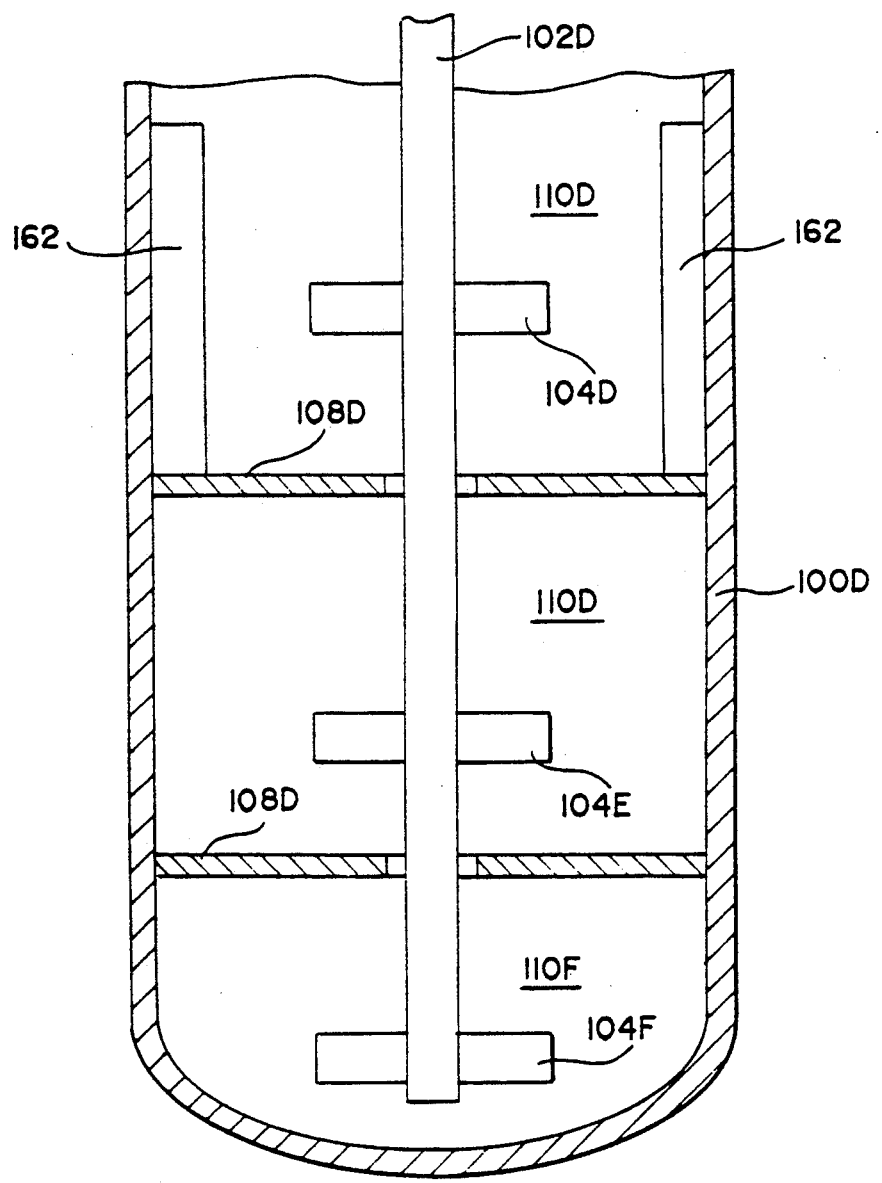
FIG. 3 is a partially fragmented detailed drawing presenting one preferred embodiment of the apparatus shown in FIG. 2 as part of the overall system.

Yet another aspect or feature of the present invention provides means for effecting desired disentrainment within the three-compartment continuous stirred tank reactors shown, for example, in FIG. 2. As further illustrated in FIG. 3, a three-compartment continuous stirred tank reactor 100D can be provided with substantially vertical, i.e., upstanding, baffles in some of the compartments. The apertures in partitions 108D are in substantial registry so as to accommodate impeller shaft 102D therethrough. In particular, it has been observed that a desired liquid hold-up and aeration can be achieved in each of the compartments 110D, 110E and 110F by incorporating upstanding baffles 162 in at least one of the downstream compartments, usually in the uppermost or downstream-most compartment 110D. The absence of baffles from the intermediate compartment 110E and lowermost or upstream-most compartment 110F enables impeller blades 104E and 104F affixed to the agitator shaft 102D, to circulate the contents of the intermediate and lowermost compartments 110E and 110F relative to the inner surface of the reactor 100D. Such circulation of the contents, in turn, generates centrifugal force fields within the intermediate and lowermost compartments 110E and 110F.

Thus, in operation, rotation of the impeller blades 104E and 104F relative to the reactor 100D causes the liquid portion of the reactor contents (generally, a gas-in-liquid dispersion) to be urged radially outwardly from agitator shaft 102D while the gas (or vapor) portions of the reactor contents are free to pass upwardly from one reactor compartment to the next reactor compartment, thereby effecting disentrainment of the liquid portion of the reactor contents from the vapor (or gaseous) portion within the intermediate and lowermost compartments 110E and 110F. This is highly desirable from a processing standpoint. Such an arrangement, it has been observed, tends to concentrate the gaseous (or vapor) portion of the reactor contents (a liquid-in-gas-dispersion) located generally near the central axis of the reactor compartment to the next because of the provided gap or aperture between the agitator shaft 102D and the horizontal partitions or dividers 108D. At the same time, and because the liquid-in-gas dispersion is passing through the rotating impeller blades of the agitator shaft, the excess entrained liquid is effectively knocked back by centrifugal fields, impellers 104E in the intermediate compartment 110E are preferably of the axial-downflow type. Impellers 104F in the lowermost compartment 110F are of the so-called "straight-blade" type, which generally cause the gas-in-liquid dispersion in the lowermost compartment 110F to be urged radially outwardly from agitator shaft 102D.

A feature of the present invention will now be discussed with reference to FIG. 2. In the production of other aromatic carboxylic acids, such as liquid-phase oxidation of meta-xylene to produce isophthalic acid and liquid-phase oxidation of para-xylene to produce terephthalic acid, it has been discovered that it is desirable to add the alkylaromatic feed not only to the lowermost compartment via feed pipe 114B but also to the intermediate compartment via feed pipe 164B, or to the uppermost compartment via feed pipe 166B, or to both such compartments as desired. To that end, the several feed pipes 114B, 164B and 166B are each provided with a separate automatic flow control valve 168B, 170B and 172B, each of which is operatively connected to a flow-control system 148B.

As mentioned above, the partially-reacted liquid reaction mixture that is discharged from the uppermost compartment of the first reactor 100B is passed via discharge pipe 152 to transfer pump 154 which, in turn, supplies the partially-reacted liquid reaction mixture into the lowermost compartment of the second reactor 100C via the inlet line 156. It is desirable to add the partially-reacted liquid reaction mixture not only to the lowermost compartment via inlet line 156 but also to the intermediate compartment via feed pipe 164C or to the uppermost compartment via feed pipe 166C, or to both such compartments as desired. To that end, the several feed pipes 156C, 164C and 166C are each provided with a separate automatic flow control valve 168C, 170C and 172C each of which is operatively connected to a separate flow-control system 148C.

From the terminal compartment of the second reactor 100C, the product-containing reaction mixture is passed via discharge pipe 174 to the product collection site 126, for further processing, as desired.

The following examples are provided to illustrate some of the preferred embodiments of the present invention but are not intended to limit the scope of the present invention.

EXAMPLE 1

The continuous oxidation of p-xylene to terephthalic acid was carried out in a reactor having a single horizontal divider plate forming two compartments. The volume of the lower compartment was about 4.8 liters. The liquid level in the upper compartment was adjusted to give an effective volume of about 4.8 liters. A liquid feed stream consisting of 3320 g/hr acetic acid, 1470 g/hr p-xylene, 66.3 g/hr water, 7.25 g/hr cobalt acetate tetrahydrate, 18.5 g/hr manganese acetate tetrahydrate and 8.83 g/hr of a 48 percent HBr solution in water was continuously fed to the bottom compartment. Air was continuously fed to the bottom compartment at a rate of 180 SCFH. The liquid product was continuously withdrawn from the top compartment. The off gas passed through a downflow condenser and through a back pressure control valve. The top compartment was maintained at the desired temperature by adjusting the reactor pressure. The bottom compartment was maintained at the desired temperature by apportioning the liquid reflux between the two compartments. Run conditions and experimental results are shown in Table 1.

EXAMPLE 2 p-Xylene was oxidized as in Example 1 except that only 70 percent of the total p-xylene was added to the bottom compartment, with the balance being added to the top compartment. Compared to Example 1, the conversion increased, as evidenced by the lower contents of 4-carboxybenzaldehyde and p-toluic acid in the product slurry. There was no increase in carbon oxides production, which is normally seen when the conversion is increased by such means as increasing temperature or catalyst concentration.

EXAMPLE 3 p-Xylene was oxidized as in Example 1 except that only 50 percent of the total bromine was added to the bottom compartment, with the balance being added to the top compartment. Compared to Example 1, the production of benzoic acid was reduced. Benzoic acid is undesirable because it builds up when mother liquor is recycled to the reactor, and it contributes to the formation of colored and fluorescent by-products.

TABLE 1

| | Oxidation of Para-xylene | | |
|---|---|---|---|
| Example | 1 | 2 | 3 |
| Temperatures, °F.: | | | |
| Top Compartment | 383 | 383 | 385 |
| Bottom Compartment | 338 | 338 | 340 |
| Reactor Pressure, psig | 222 | 223 | 222 |
| Oxygen Concentration in Vent Gas, % | 2.94 | 2.93 | 2.96 |
| Moles CO/(Mole pX) | 0.027 | 0.028 | 0.027 |
| Moles $CO_2$/(Mole pX) | 0.118 | 0.120 | 0.109 |
| Product Slurry Analyses: | | | |
| Optical Density (340 nm) | 12.5 | 10.4 | 10.3 |
| Benzoic Acid, Weight % | 0.096 | 0.016 | 0.069 |
| 4-Carboxybenzaldehyde, Weight % | 1.10 | 0.86 | 1.08 |
| p-Toluic Acid, Weight % | 2.58 | 1.84 | 2.65 |

EXAMPLE 4

The continuous oxidation of m-xylene to isophthalic acid was carried out in the same reactor as used in Example 1. A liquid feed stream consisting of 5710 g/hr acetic acid, 1265 g/hr m-xylene, 530 g/hr water, 5.18 g cobalt acetate tetrahydrate, 15.6 g manganese acetate tetrahydrate and 5.16 g of a 48 percent solution of HBr in water was continuously fed to the bottom compartment. Air was continuously fed to the bottom compartment at a rate of 166 SCFH. The liquid product was continuously withdrawn from the top compartment. The off gas passed through a downflow condenser and through a back pressure control valve. The top compartment was maintained at the desired temperature by adjusting the reactor pressure. The bottom compartment was maintained at the desired temperature by apportioning the liquid reflux between the two compartments. Run conditions and experimental results are shown in Table 2.

EXAMPLE 5 m-Xylene was oxidized as in Example 4 except that only half of the total bromine was added to the bottom compartment, with the balance being fed to the top compartment. Compared to Example 4, the optical density, carbon oxides and benzoic acid were reduced. Benzoic acid is undesirable because it builds up when mother liquor is recycled to the reactor, and it contributes to the formation of colored and fluorescent by-products. Lower values for optical density, a measure of colored impurities, are preferred.

EXAMPLE 6 m-Xylene was oxidized as in Example 4 except that only 62 percent of the total m-xylene was fed to the bottom compartment, with the balance being fed to the top compartment. Compared to Example 4, both the yield of carbon oxides and the optical density were reduced.

TABLE 2

| | Oxidation of Meta-xylene | | |
|---|---|---|---|
| Example | 4 | 5 | 6 |
| Temperatures, °F.: | | | |
| Top Compartment | 417 | 418 | 417 |

TABLE 2-continued

| | Oxidation of Meta-xylene | | |
|---|---|---|---|
| Example | 4 | 5 | 6 |
| Bottom Compartment | 368 | 378 | 376 |
| Reactor Pressure, psig | 332 | 325 | 350 |
| Oxygen concentration in Vent Gas, % | 2.20 | 2.38 | 2.33 |
| Yields, Mole % Based on Xylene Feed: | | | |
| m-Toluic Acid | 6.90 | 4.30 | 5.48 |
| 3-Carboxybenzaldehyde | 1.92 | 1.30 | 1.61 |
| Carbon Oxides | 1.92 | 1.75 | 1.67 |
| Benzoic Acid | 0.67 | 0.53 | 0.72 |
| Slurry Optical Density (340 nm) | 15.0 | 11.0 | 10.3 |

EXAMPLE 7

The same reactor was used as in Example 1 except that no divider plate was used, i.e., there was only a single compartment. Vortex-breaking baffles were used. A liquid feed was continuously added at the rate of 2350 g/hr pseudocumene, 4230 g/hr acetic acid, 220 g/hr water, 19.0 g/hr cobalt (as the acetate tetrahydrate), 5.7 g/hr manganese (as the acetate tetrahydrate), 29.9 g/hr bromine (as a 48 percent solution of HBr in water) and 0.54 g/hr zirconium (as zirconium acetate). Air was added at the rate of 300 SCFH. The liquid product was continuously withdrawn from the reactor. The off gas passed through a downflow condenser and a back pressure valve. The liquid condensate was returned to the reactor. The reactor temperature was controlled by adjusting the pressure. The results are shown in Table 3. The production of carbon oxides was very high. Moreover, it was found impossible to increase the conversion of pseudocumene significantly beyond about 70 percent, even with drastic increases in temperature.

EXAMPLE 8

The same two-compartment reactor as in Example 1 was used. Vortex-breaking baffles were used in both compartments. The liquid and air feed rates were the same as in Example 7. The results are shown in Table 3. Although the overall pseudocumene conversion was slightly higher than in Example 7, the carbon oxides production was much lower.

EXAMPLE 9

The same reactor as in Example 1 was used except that two horizontal divider plates were installed to give three compartments. Vortex-breaking baffles were used in all three compartments. The volume of the bottom compartment was approximately 2.4 liters. The volumes of the middle and upper compartments were approximately 3.6 liters each. The liquid feed rates were the same as in Example 7. The air feed rate was 170 SCFH to the lower compartment and 130 SCFH to the middle compartment. The condensate reflux rates to the middle and lower compartments were apportioned such as to hold the temperatures of these compartments at the desired level. The results are shown in Table 3. The carbon oxides production was even lower than with the two-compartment reactor of Example 8.

EXAMPLE 10

The same reactor as in Example 9 was used except that no vortex-breaking baffles were used in the middle and bottom compartments. The upper compartment did contain vortex-breaking baffles. Thus the liquid in the lower compartments was allowed to rotate. Model experiments in a Plexiglas reactor using air and water showed that the centrifugal forces generated by the rotation reduce entrainment of liquid into the next compartment, improving the liquid hold-up in the compartment. A liquid feed was continuously added to the bottom compartment at the rate of 2350 g/hr pseudocumene, 4230 g/hr acetic acid, 220 g/hr water, 19.0 g/hr cobalt (as the acetate tetrahydrate), 4.1 g/hr manganese (as the acetate tetrahydrate), 29.9 g/hr bromine (as a 48 percent solution of HBr in water) and 0.54 g/hr zirconium (as zirconium acetate). Air was added to the bottom compartment at the rate of 300 SCFH. The liquid product was continuously withdrawn from the reactor. The off gas passed through a downflow condenser and a back pressure valve. The liquid condensate was returned to the reactor. The temperature of the upper compartments was controlled by adjusting the pressure. The temperatures of the middle and lower compartments were controlled by adjusting the amount of condensate reflux returned to these compartments. The results are shown in Table 3. The production of carbon oxides was even lower than in Example 9.

TABLE 3

| Oxidation of Pseudocumene | | | | |
|---|---|---|---|---|
| Example | 7 | 8 | 9 | 10 |
| No. of Compartments | 1 | 2 | 3 | 3 |
| Baffles in Lower Compartments | Yes | Yes | Yes | No |
| Temperature, °F.: | | | | |
| Top | | | 314 | 327 | 354 |
| Middle | 342 | | 307 | 315 |
| Bottom | | 340 | 276 | 296 |
| Pseudocumene Conversion, Percent: | | | | |
| Overall | | 62.6 | 65.6 | 65.9 | 66.3 |
| To Carbon Oxides | | 4.38 | 2.91 | 2.79 | 2.63 |

EXAMPLE 11

Four reaction stages were obtained by connecting two two-compartment reactors as described in Example 1 in series. A positive displacement pump was used to transport the effluent from the top compartment of the first reactor to the bottom compartment of the second reactor. The pumping rate was adjusted to keep the liquid in the top compartment of the first reactor at the desired level. All of the liquid feed was added to the bottom compartment of the first reactor. The air feed was split between the bottom of the first reactor and the bottom of the second reactor. Run conditions and experimental results are shown in Table 4. The low content of methyl di-acids (4-methyl isophthalic acid, 2-methyl terephthalic acid and 4-methyl orthophthalic acid, which are reaction intermediates) shows that the reaction went essentially to completion. The product analyses are similar to those obtained from batch oxidations.

EXAMPLE 12

Pseudocumene was oxidized in a manner similar to that of Example 11 except that additional (tailout) catalyst was added. The tailout catalyst metals were equally split between the second, third and fourth compartment. The tailout bromine was evenly split between the second and third compartments. Run conditions and experimental results are shown in Table 4. The methyl di-acids were even lower than in Example 11.

EXAMPLE 13

Six reaction stages were obtained by connecting two three-stage reactors as described in Example 10 in series. A positive displacement pump was used to transport the effluent from the top compartment of the first reactor to the bottom compartment of the second reactor. The pumping rate was adjusted to keep the liquid in the top compartment of the first reactor at the desired level. Run conditions and experimental results are shown in Table 4. Note that the pseudocumene feed was split evenly between the first two compartments. The oxidation intermediates (methyl di-acids) in the product cake were very low.

TABLE 4

| Oxidation of Pseudocumene in Four and Six-Stage Reactors | | | |
|---|---|---|---|
| Example | 11 | 12 | 13 |
| Feed Rates, g/hr: | | | |
| Pseudocumene to First Compartment | 5440 | 5440 | 2720 |
| Pseudocumene to Second Compartment | 0 | 0 | 2720 |
| Acetic Acid | 9770 | 9770 | 9770 |
| Water | 515 | 515 | 515 |
| Initial Catalyst, Weight % Based on Pseudocumene: | | | |
| Co | 0.28 | 0.28 | 0.28 |
| Mn | 0.060 | 0.088 | 0.088 |
| Br | 0.44 | 0.28 | 0.263 |
| Zr | 0.008 | 0.010 | 0.010 |
| Tailout Catalyst, Weight % Based on Pseudocumene: | | | |
| Mn | 0 | 0.011 | 0.023 |
| Br | 0 | 0.13 | 0.263 |
| Zr | 0 | 0.006 | 0.011 |
| First Reactor: | | | |
| Residence Time, min | 38.5 | 46.4 | 48.0 |
| Air Feed Rate, SCFH | 267 | 264 | 250 |
| Bottom Temperature, °F. | 316 | 316 | 305 |
| Middle Temperature, °F. | | | 338 |
| Top Temperature, °F. | 336 | 336 | 368 |
| Pseudocumene Conversion, Percent | 71.5 | 70.4 | 72.0 |
| Carbon Oxides, Mole % of Pseudocumene Fed | 4.16 | 4.26 | 5.29 |
| Second Reactor: | | | |
| Residence Time, min | 46.2 | 56.1 | 45.7 |
| Air Feed Rate, SCFH | 124 | 127 | NA |
| Bottom Temperature, °F. | 371 | 365 | 362 |
| Top Temperature, °F. | 385 | 381 | 384 |
| Pseudocumene Conversion, Percent | 26.6 | 26.8 | 392 |
| Carbon Oxides, Mole % of Pseudocumene Fed | 4.26 | 8.60 | 4.51 |
| Dry Cake Analysis, Weight %: | | | |
| Methyl Di-Acids | 0.644 | 0.138 | 0.093 |
| Di-Acids | 2.176 | 1.952 | 1.808 |
| Trimellitic Acid | 91.59 | 93.66 | 91.16 |
| Normalized Trimellitic Acid Yield | 86.3 | 87.4 | 85.8 |

These examples demonstrate the advantages that are obtained by using the method and apparatus of the present invention for the oxidation of the alkylaromatic to the corresponding carboxylic or polycarboxylic acids.

What has been illustrated and described herein is a method and an apparatus for continuously oxidizing an aromatic alkyl in the liquid phase and under oxidation-reaction conditions to produce an aromatic carboxylic acid product. While the method and apparatus of the present invention have been illustrated and described with reference to several preferred embodiments, the present invention is not limited thereto. Alternatives, changes and modifications are possible and will become apparent to those skilled in the art upon reference to the foregoing description and the drawings. Accordingly, such alternatives, changes and modifications form a part of the invention insofar as they fall within the spirit and scope of the appended claims.

We claim:

1. A method for continuously oxidizing an alkylaromatic in the liquid phase and under oxidation-reaction conditions to produce an aromatic carboxylic acid, comprising the steps of:

sequentially passing at least a portion of a reaction mixture including the alkylaromatic through a plurality of series-arranged walled but communicating compartments of a reactor means maintained under predetermined oxidation-reaction conditions, from an initial one of the series-arranged walled plural compartments downstream to a terminal one thereof, introducing the remainder portion of the reaction mixture into another one of the series-arranged walled plural compartments downstream from the initial compartment, and passing said remainder portion to the terminal compartment while agitating the contents of each of the walled plural compartments and producing in each of the walled plural compartments an aromatic carboxylic acid-containing liquid phase and a gaseous phase; at least a portion of the walls of said series-arranged compartments being apertured to enable passage of the reaction mixture through the reactor means from the initial one of the series-arranged plural compartments to the terminal one thereof;

withdrawing from the terminal compartment a portion of the gaseous phase contained therein;

condensing at least a portion of the thus-withdrawn gaseous phase to produce a liquid stream; and returning at least a portion of the thus-condensed liquid stream to preselected ones of the walled plural compartments to maintain a preselected liquid-phase temperature differential between the terminal and initial compartments of the reactor.

2. The method of claim 1 wherein the alkylaromatic is pseudocumene and wherein the aromatic carboxylic acid is trimellitic acid.

3. The method of claim 1 wherein the alkylaromatic is para-xylene and wherein the aromatic carboxylic acid is terephthalic acid.

4. The method of claim 1 wherein the alkylaromatic is meta-xylene and wherein the aromatic carboxylic acid is isophthalic acid.

5. The method of claim 1 wherein the reaction mixture further includes a catalyst and an oxygen-containing gas.

6. The method of claim 1 wherein the reaction mixture includes a solvent.

7. The method of claim 5 wherein the reaction mixture includes acetic acid and water.

8. The method of claim 1 wherein adjacent ones of the series-arranged walled plural compartments are in phase communication with one another.

9. The method of claim 1 wherein the liquid phase is a gas-in-liquid dispersion and wherein the gaseous phase is a liquid-in-gas dispersion.

10. The method of claim 1 wherein the thus-condensed liquid stream is apportioned and returned to the walled plural compartments so as to maintain a corresponding plurality of preselected liquid-phase temperature differentials among the compartments.

11. The method of claim 1 further comprising circulating the contents of each of the walled plural compartments relative to the reactor so as to disentrain the liquid phase from the gaseous phase within at least one of the walled plural compartments.

12. The method of claim 1 wherein the series-arranged plural compartments include an intermediate walled compartment, relative to the flow of the reaction mixture through the reactor means, wherein a portion of the reaction mixture is sequentially passed through the plurality of series-arranged walled compartments, and wherein the remainder of the reaction mixture is introduced into the intermediate walled compartment and is sequentially passed downstream from said intermediate walled compartment to the terminal one of the plural walled compartment.

13. The method of claim 12 wherein the intermediate walled compartment is contiguous with the initial walled compartment.

14. The method of claim 13 wherein the intermediate walled compartment is contiguous with the terminal walled compartment.

15. The method of claim 1 wherein the reaction mixture comprises a solvent, catalyst metals, a bromine source, an oxidizing gas and an alkylaromatic, wherein the solvent, catalyst metals, bromine source, oxidizing gas and alkylaromatic are each independently apportioned in preselected amounts to each of the series-arranged walled but communicating compartments.

16. The method of claim 15 wherein all or essentially all of the solvent, and all or essentially all of the catalyst metals and bromine source are added to the initial one of the series-arranged walled but communicating compartments and wherein the alkylaromatic is apportioned to at least one of the series-arranged walled but communicating compartments.

* * * * *